United States Patent
Nelson et al.

(10) Patent No.: US 7,360,999 B2
(45) Date of Patent: Apr. 22, 2008

(54) MEANS FOR USING SINGLE FORCE SENSOR TO SUPPLY ALL NECESSARY INFORMATION FOR DETERMINATION OF STATUS OF MEDICAL PUMP

(75) Inventors: Steven R. Nelson, Grove City, OH (US); Chad E. Bouton, Delaware, OH (US); Dale M. Radcliff, Dublin, OH (US); Roger W. Smith, Grove City, OH (US); Clark E. Fortney, Gahanna, OH (US)

(73) Assignee: Abbott Laboratories, Abbott Park, IL (US)

( * ) Notice: Subject to any disclaimer, the term of this patent is extended or adjusted under 35 U.S.C. 154(b) by 689 days.

(21) Appl. No.: 10/624,578

(22) Filed: Jul. 22, 2003

(65) Prior Publication Data

US 2004/0247445 A1 Dec. 9, 2004

Related U.S. Application Data

(60) Provisional application No. 60/418,986, filed on Oct. 16, 2002, provisional application No. 60/418,914, filed on Oct. 16, 2002.

(51) Int. Cl.
*F04B 49/00* (2006.01)
*F04B 43/02* (2006.01)
*A61M 31/00* (2006.01)

(52) U.S. Cl. .......................... 417/63; 417/479; 604/67; 604/153

(58) Field of Classification Search .................. 417/63, 417/478, 479, 477.2; 604/153, 67, 31
See application file for complete search history.

(56) References Cited

U.S. PATENT DOCUMENTS

| | | | | |
|---|---|---|---|---|
| 4,322,201 A | * | 3/1982 | Archibald | 417/279 |
| 4,453,931 A | | 6/1984 | Pastrone | |
| 4,840,542 A | * | 6/1989 | Abbott | 417/9 |
| 4,927,411 A | | 5/1990 | Pastrone et al. | |
| 5,056,992 A | | 10/1991 | Simons et al. | |
| 5,464,392 A | | 11/1995 | Epstein et al. | |
| 5,554,013 A | | 9/1996 | Owens et al. | |
| 6,656,148 B2 | | 12/2003 | Das et al. | |
| 6,659,980 B2 | | 12/2003 | Moberg et al. | |
| 2002/0128594 A1 | * | 9/2002 | Das et al. | 604/67 |

* cited by examiner

*Primary Examiner*—Charles G Freay
(74) *Attorney, Agent, or Firm*—Thomas D. Brainard; David L. Weinstein

(57) ABSTRACT

A medical pump, for use with a cassette having a pumping chamber, includes a pumping element with a piston slider assembly which intermittently pressurizes the pumping chamber during a pumping cycle and has a piston head connected to a main body with a single pressure sensor positioned therebetween. A camshaft is associated with the pumping element, an inlet control element, and an outlet control element for closing the pumping chamber to flow when the pumping chamber is pressurized. A processing unit receives pressure and position data from the pressure sensor and a position sensor associated with the pumping element, and processes this data to determine the operating condition of the pump. The operating conditions determined include: blocked fluid flow, no fluid in the line, no cassette associated with the pump, proper pump priming, or proper valve sealing.

20 Claims, 13 Drawing Sheets

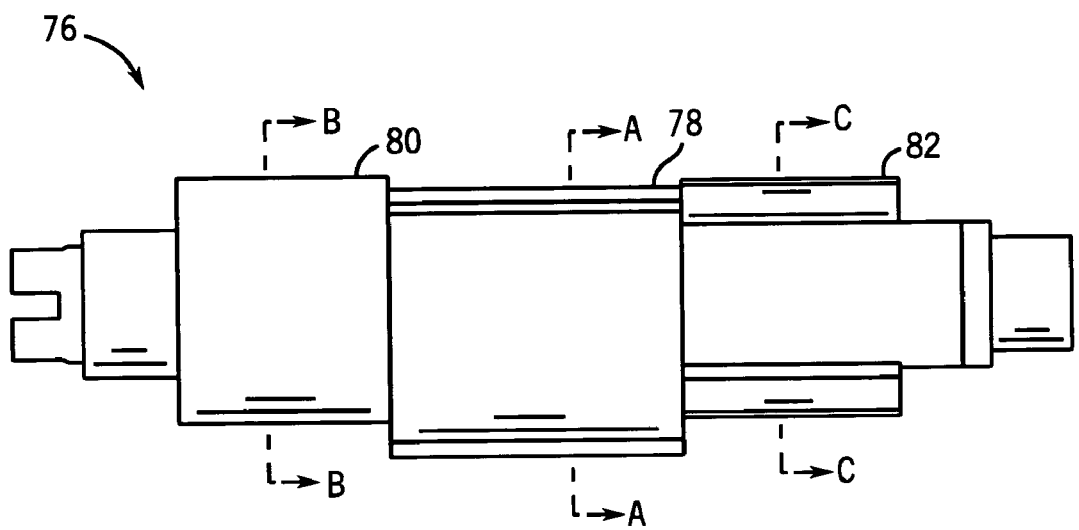
FIG. 7
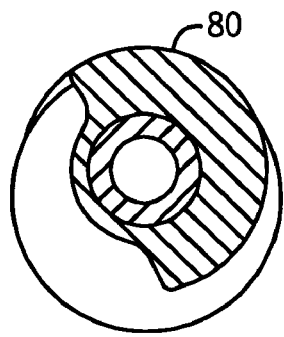
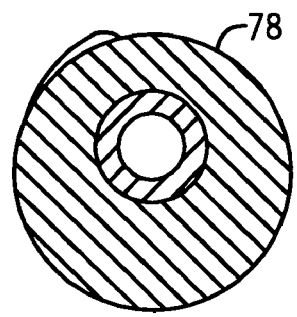
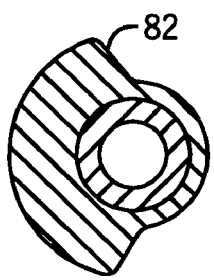
FIG. 9  FIG. 8  FIG. 10

MEANS FOR USING SINGLE FORCE SENSOR TO SUPPLY ALL NECESSARY INFORMATION FOR DETERMINATION OF STATUS OF MEDICAL PUMP

CROSS-REFERENCE TO RELATED APPLICATIONS

This application claims the benefit of U.S. Provisional Application No. 60/418,986, filed on Oct. 16, 2002, and of U.S. Provisional Application No. 60/418,914, filed on Oct. 16, 2002.

BACKGROUND OF THE INVENTION

The present invention relates to a means of determining the operating condition of a medical pump. More particularly, this invention relates to a means of determining fluid status in positive displacement fluid pumping devices for the delivery of fluids to a patient.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. Of the modern medical pumps, those incorporating a diaphragm or pump cassette are often preferred because they provide a more accurate controlled rate and volume than do other types of pumps.

A typical positive displacement pump system includes a pump device driver and a disposable cassette. The disposable cassette, which is adapted to be used only for a single patient and for one fluid delivery cycle, is typically a small plastic unit having an inlet and an outlet respectively connected through flexible tubing to the fluid supply container and to the patient receiving the fluid. The cassette includes a pumping chamber, with the flow of fluid through the chamber being controlled by a plunger or pumping element 38 activated in a controlled manner by the device driver.

For example, the cassette chamber may have one wall formed by a flexible diaphragm which is reciprocated by the plunger and the driver to cause fluid to flow. The pump driver device includes the plunger or pumping element 38 for controlling the flow of fluid into and out of the pumping chamber in the cassette, and it also includes control mechanisms to assure that the fluid is delivered to the patient at a pre-set rate, in a pre-determined manner, and only for a particular pre-selected time or total dosage.

The fluid enters the cassette through an inlet and is forced through an outlet under pressure. The fluid is delivered to the outlet when the pump plunger forces the membrane into the pumping chamber to displace the fluid. During the intake stroke the pump plunger draws back, the membrane covering the pumping chamber pulls back from its prior fully displaced configuration, and the fluid is then drawn through the open inlet and into the pumping chamber. In a pumping stroke, the pump plunger forces the membrane back into the pumping chamber to force the fluid contained therein through the outlet. Thus, the fluid flows from the cassette in a series of spaced-apart pulses rather than in a continuous flow.

One of the requirements for a medical pump is that it is able to detect when it is operating under certain abnormal situations and to alert the user to these problems. Specifically, the pump should detect when flow of fluid is blocked, there is no fluid in the line, there is no cassette in the pump, if the pump has primed correctly, and if the valves in the pump are sealing properly.

Previous pumps that could supply all this information used at least two sensors associated with the pumping chamber or tubes to provide input regarding the fluid conditions to the control system. The use of multiple sensors requires more physical space on the pump and potentially results in a higher unit manufacturing cost.

It is therefore a principal object of this invention to provide means for using a single pressure sensor to discriminate between operating conditions in a medical pump.

These and other objects will be apparent to those skilled in the art.

SUMMARY OF THE INVENTION

A medical pump, for use with a cassette having a pumping chamber, is disclosed. The pump includes a pumping element with a piston slider assembly which intermittently pressurizes the pumping chamber during a pumping cycle. The piston slider assembly has a piston head connected to a main body with a single pressure sensor positioned therebetween. A camshaft is associated with the pumping element, an inlet control element, and an outlet control element for closing the pumping chamber to flow when the pumping chamber is pressurized. A position sensor detects the position of the pumping element. A processing unit receives pressure and position data from the pressure and position sensors. The processing unit processes this data to determine the operating condition of the pump. The operating conditions determined include: blocked fluid flow, no fluid in the line, no cassette associated with the pump, proper pump priming, or proper valve sealing.

DESCRIPTION OF THE DRAWINGS

FIG. 7 is a side view of the camshaft of the present invention;

FIG. 8 is a sectional view taken along line A-A of FIG. 7, showing the piston lobe of the camshaft of the present invention;

FIG. 9 is a sectional view taken along line B-B of FIG. 7, showing the inlet lobe of the camshaft of the present invention;

FIG. 10 is a sectional view taken along line C-C of FIG. 7, showing the outlet lobe of the camshaft of the present invention;

DETAILED DESCRIPTION OF THE PREFERRED EMBODIMENT

Figure 1:
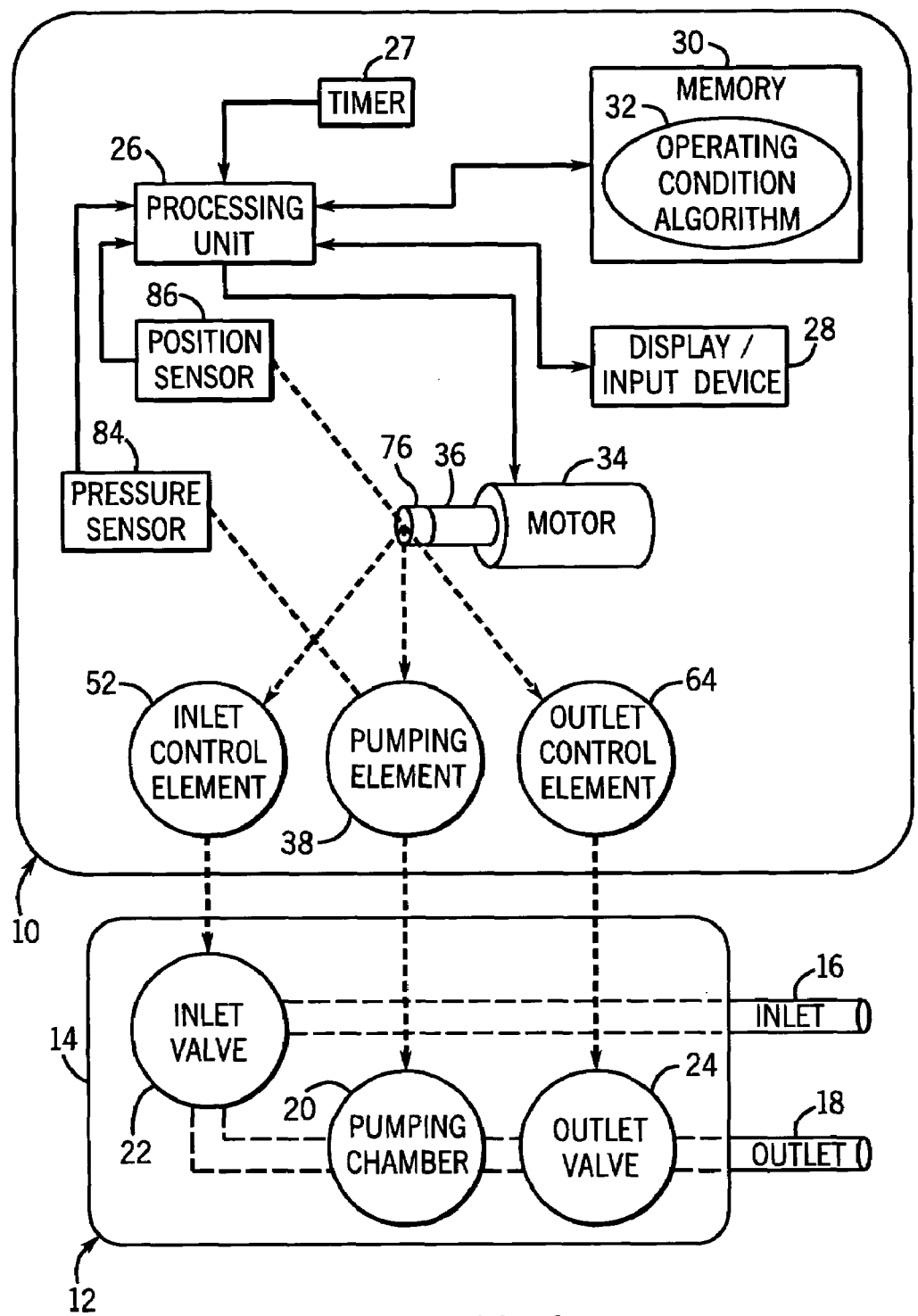
FIG. 1 is a schematic diagram of the cassette pump, illustrating the functional components of the pump and the cassette.

FIG. 1 is a schematic diagram illustrating the functional components of a medical pump 10 which is used in connection with a disposable cassette 12 for delivering a fluid to a patient. It will be understood to one of ordinary skill in the art that the term medical pump as used herein includes but is not limited to enteral pumps, parenteral infusion pumps, ambulatory pumps, or any positive displacement fluid pumping device for the delivery of fluids to a patient.

The medical pump 10 and cassette 12 are shown with several components for implementing the present invention. Those of ordinary skill in the art will appreciate that the pump 10 and cassette 12 include many more components than those shown in FIG. 1. However, it is not necessary that all these components be shown in order to disclose an illustrative embodiment for practicing the present invention. Commonly assigned and co-pending non-provisional application U.S. Ser. No. 29/166,389 entitled PUMP CASSETTE discloses the particular cassette 12 described below. Pump cassettes and cassette pumps in general are well known in the art of medical fluid delivery, as evidenced by commonly assigned U.S. Pat. Nos. 4,818,186; 4,842,584; and 5,000,664, the entire disclosure and drawings of which are hereby specifically incorporated herein by reference.

Cassette 12 includes a housing 14 on which is disposed an inlet port 16 for accepting the fluid flowing from an IV bag or other fluid container (not shown). Similarly, fluid lines (not shown) couple an outlet port 18 on housing 14 to the body of a patient.

A pumping chamber 20 is connected in fluid flow communication between the inlet port 16 and the outlet port 18. The pumping chamber 20 operates to meter fluid through the cassette 12.

An inlet valve 22 resides between inlet port 16 and the pumping chamber 20. Inlet valve 22 operates to physically open and close the fluid communication between inlet port 16 and pumping chamber 20.

Similarly, an outlet valve 24 resides between the pumping chamber 20 and outlet port 18. Outlet valve 24 operates to physically open and close the fluid communication between pumping chamber 20 and outlet port 18. The pumping chamber 20, inlet valve 22, and outlet valve 24 are all operatively associated with the pump 10 to control the flow of fluid through the cassette 12.

Figure 2:
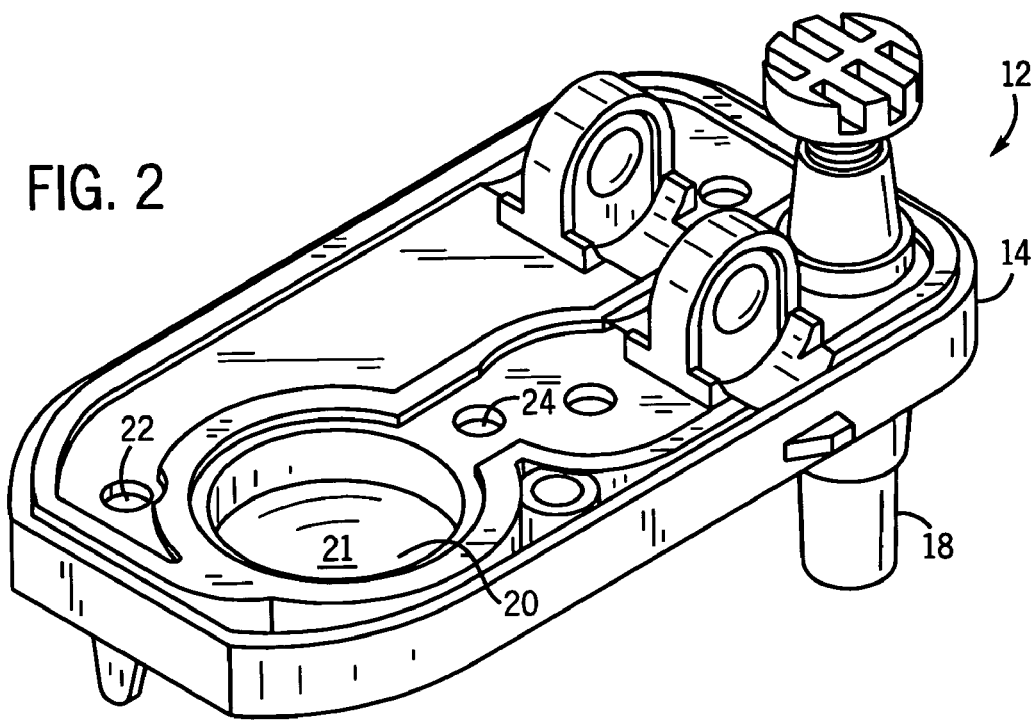
FIGS. 2 and 3 are perspective views of a cassette for use with the pump of the present invention.
Figure 3:
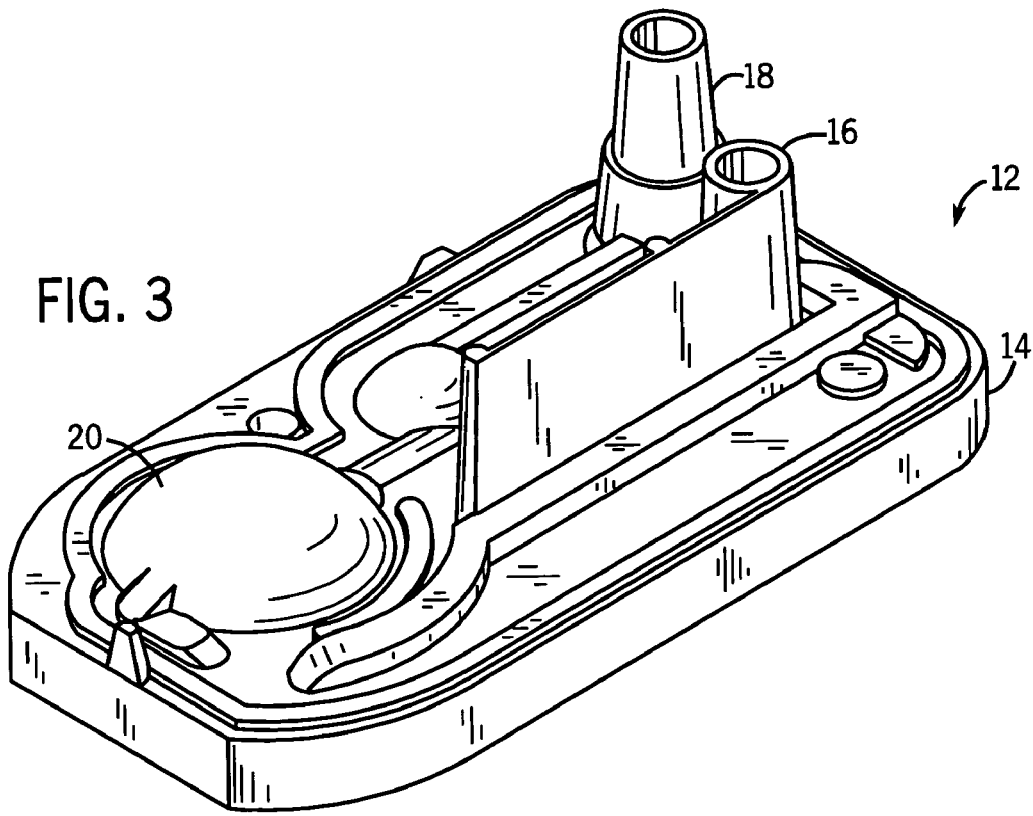

Referring to FIGS. 2 and 3, one embodiment of cassette 12 is shown. It will be understood to one of ordinary skill in the art that a cassette having a different design than that shown in FIGS. 2-3 may be used with pump 10 without departing from the present invention.

Referring to FIG. 1, a processing unit 26 is included in pump 10 and performs various operations described in greater detail below. A display/input device 28 communicates with the processing unit 26 and allows the user to receive output from processing unit 26 and/or input into the processing unit 26. Those of ordinary skill in the art will appreciate that display/input device 28 may be provided as a separate display device and a separate input device.

A memory 30 communicates with the processing unit 26 and stores code and data necessary for the processing unit 26 to calculate and output the operating conditions of pump 10. More specifically, the memory 30 stores an algorithm code 32 formed in accordance with the present invention for processing data to determine the operating condition of the pump 10.

These algorithms, Figure of Merit calculations and other details of the method for using pressure and position data to determine the operating condition of the pump 10 not discussed herein can be determined by reference to commonly assigned and co-pending non-provisional application entitled METHOD FOR DISCRIMINATING BETWEEN OPERATING CONDITIONS IN MEDICAL PUMP, which claims priority from provisional applications U.S. Ser. No. 60/418,914 and 60/418,986, the disclosure and drawings of which are hereby specifically incorporated herein by reference in its entirety. The disclosures and drawings of the provisional applications U.S. Ser. No. 60/418,986 and 60/418,914 are also specifically incorporated herein by reference in their entirety.

An electric motor 34 is controlled by processing unit 26 is energized by a power supply (not shown) to serve as a prime mover for rotatably driving a shaft 36. The motor 34 is a 6-volt, permanent magnet, DC gear motor with a 249:1 gear (not shown) on the output of the motor shaft 36. This motor 34 runs at different speeds depending on flow rates. The down-stroke or delivery portion of the stroke has the motor 34 running directly from power supply (not shown). The up-stroke, retract or fill portion of the stroke is run at a voltage set by the processing unit 26, so that the retract times are approximately 1.3, 1.4, 1.6, or 2.0 seconds, where higher flow rates require faster retract speeds.

A pumping element 38 is operatively associated with the shaft 36. When energized, the pumping element 38 reciprocates back and forth to periodically down-stroke, causing pumping element 38 to press on the diaphragm 21 of pumping chamber 20, driving fluid through cassette 12. On an up-stroke, pumping element 38 releases pressure from pumping chamber 20 and thereby drawing fluid from inlet port 16 into pumping chamber 20.

Figure 4:
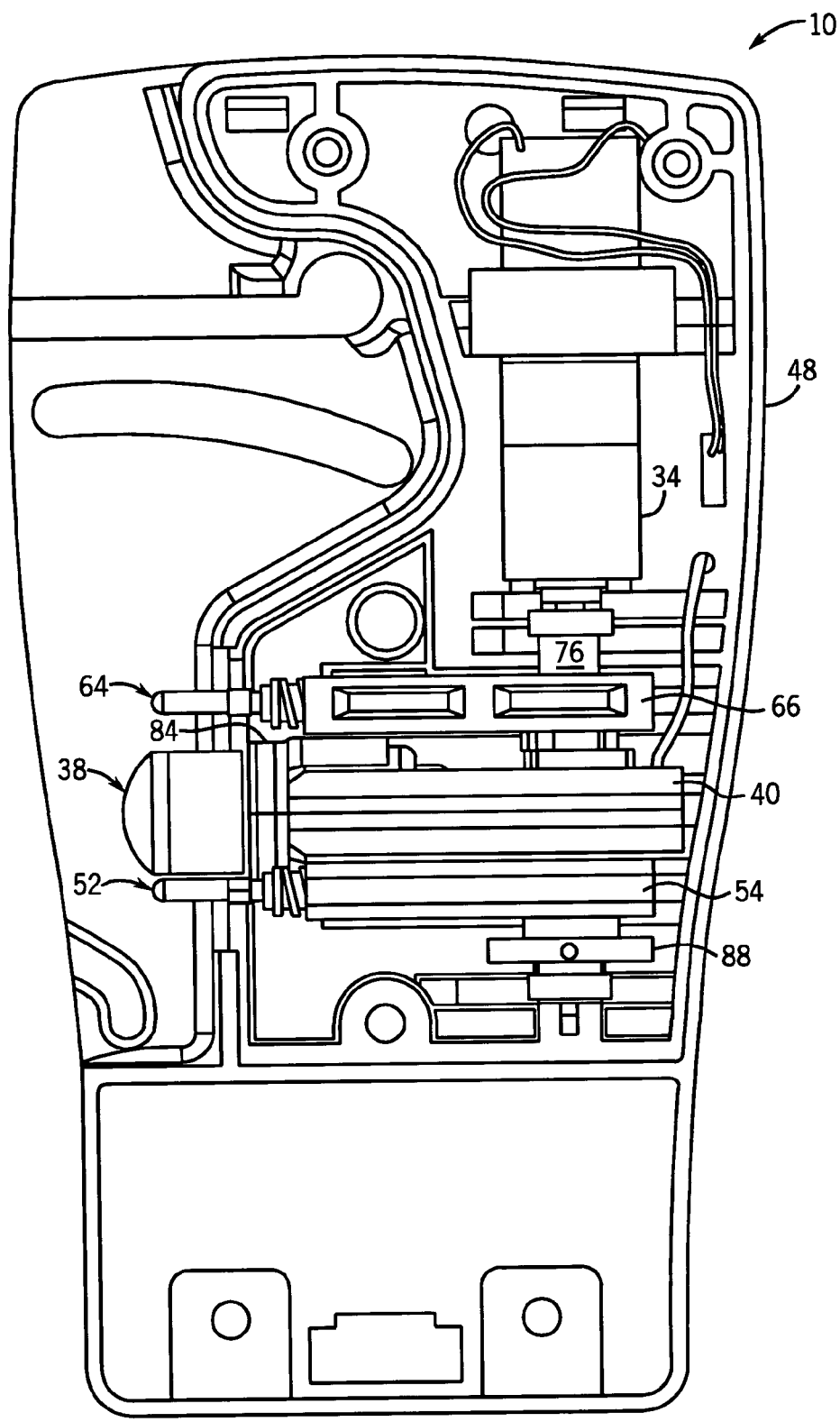
FIG. 4 is an internal side view of the pump of the present invention.
Figure 5:
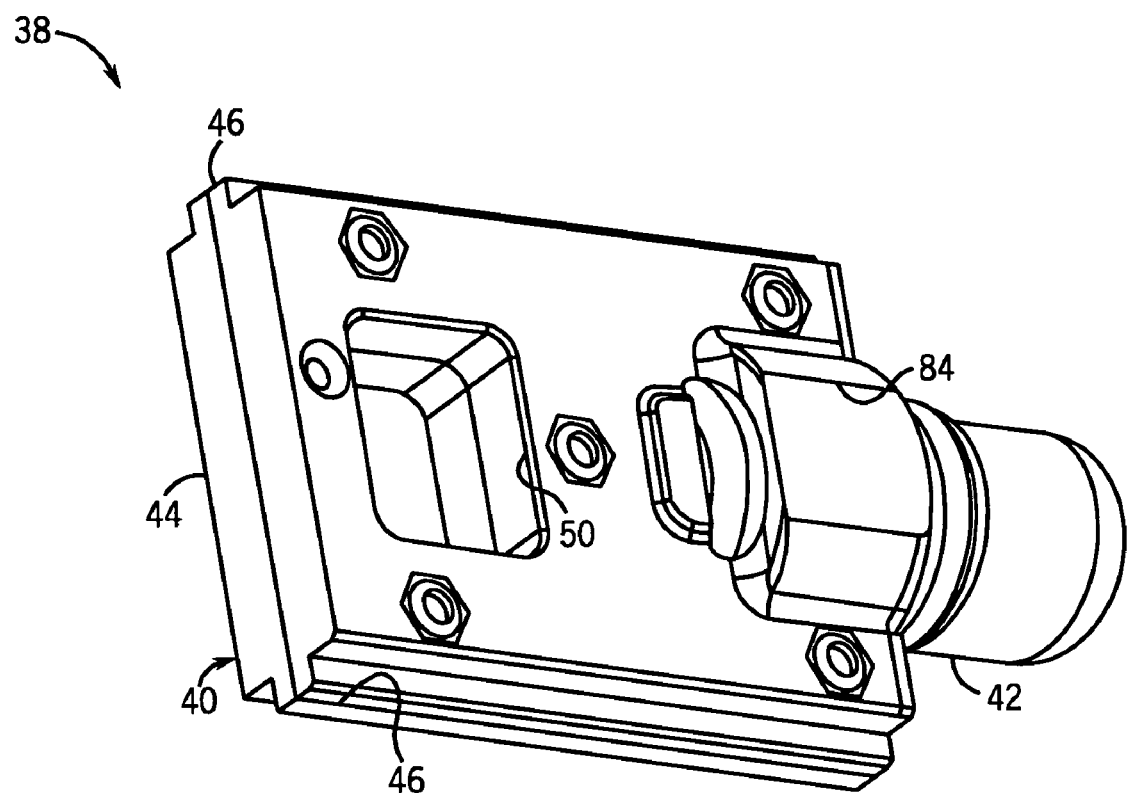
FIG. 5 is a perspective view of the pumping element of the present invention.

Referring to FIGS. 4 and 5, the pumping element 38 is formed as a piston slider assembly 40. The piston slider assembly 40 includes a piston head 42 for contacting the pumping chamber 20 connected to a main body 44. Sliders 46 permit the piston slider assembly 40 to be slidably associated with rails (not shown) within a pump housing 48. A bore 50 passes through main body 44 and provides a surface for transferring force from the motor 34 to the pumping element 38.

Referring to FIG. 1, an inlet control element 52 is operatively associated with the shaft 36. When energized, inlet control element 52 reciprocates back and forth to periodically down-stroke, causing inlet control element 52 to press on inlet valve 22, closing pumping chamber 20 to fluid influx. On an up-stroke, inlet control element 52 releases pressure from inlet valve 22 and thereby allows the flow of fluid from inlet port 16 into pumping chamber 20.

Figure 6A:
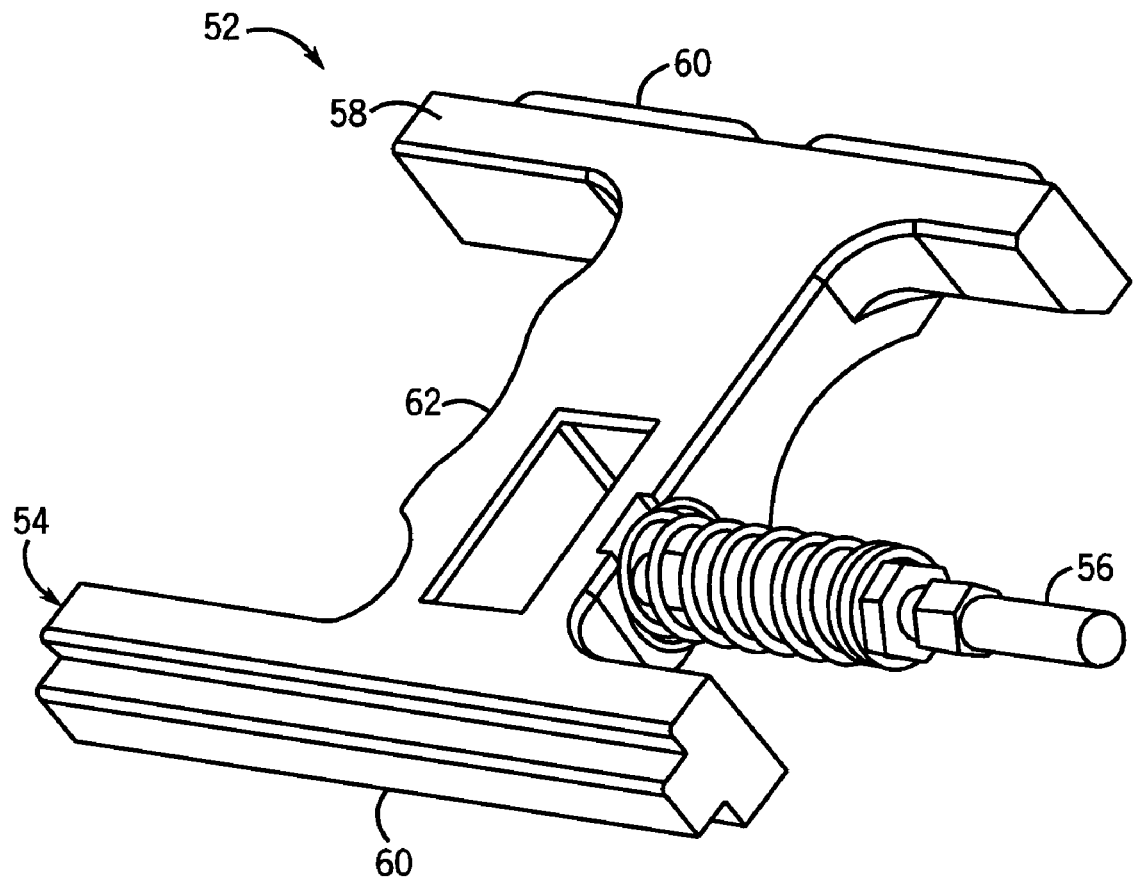
FIG. 6A is a perspective view of the inlet control element of the present invention.

Referring to FIGS. 4 and 6A, the inlet control element 52 is formed as an inlet slider assembly 54. The inlet slider assembly 54 includes an inlet pin 56 for contacting the inlet valve 22 and is connected to and spring biased against a main body 58. Sliders 60 permit the inlet slider assembly 54 to be slidably associated with rails (not shown) within pump housing 48. A notch 62 is positioned on the main body 58 to provide a surface for transferring force from the motor 34 to the inlet control element 52.

Referring to FIG. 1, an outlet control element 64 is operatively associated with the shaft 36. When energized, outlet control element 64 reciprocates back and forth to periodically down-stroke, causing outlet control element 64 to press on outlet valve 24, closing pumping chamber 20 to fluid efflux. On an up-stroke, outlet control element 64 releases pressure from outlet valve 24 and thereby allows the flow of fluid from pumping chamber 20 to outlet port 18. Thus the open or closed state of pumping chamber 20 is controlled by the positioning and movement of inlet and outlet control elements 52 and 64.

Figure 6B:
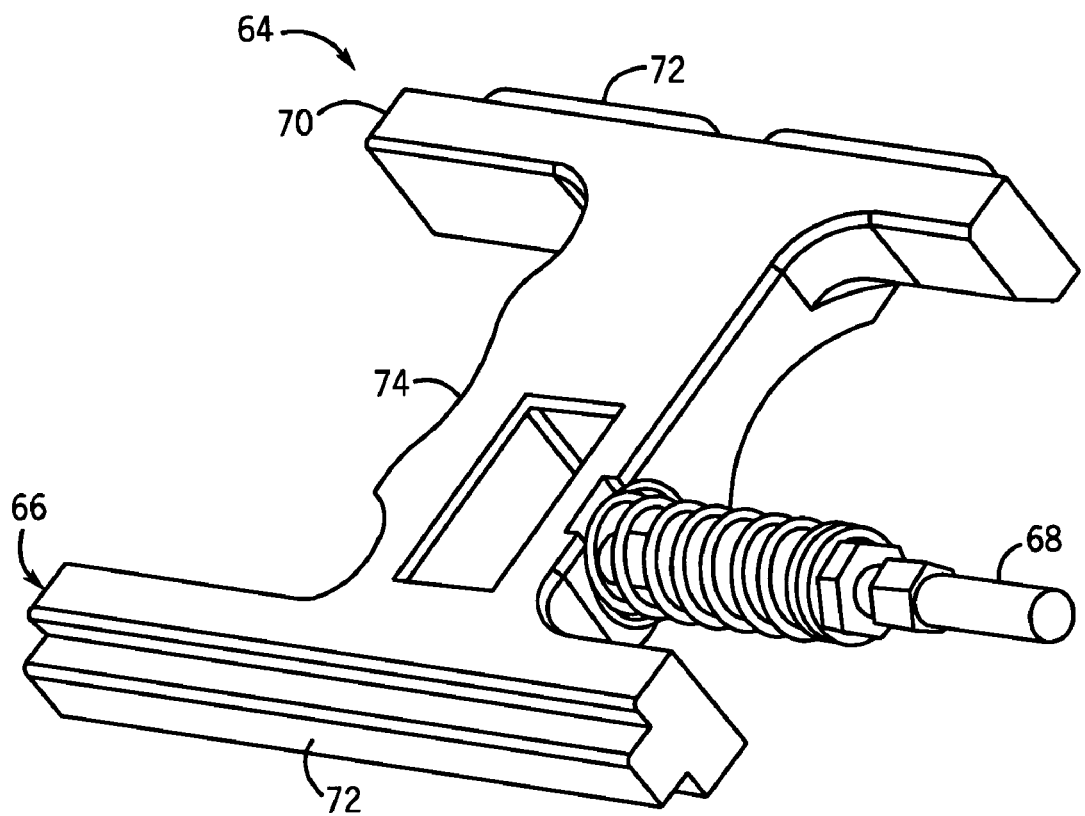
FIG. 6B is a perspective view of the outlet control element of the present invention.

Referring to FIGS. 4 and 6B, the outlet control element 64 is formed as an outlet slider assembly 66. The outlet slider assembly 66 includes an outlet pin 68 for contacting the outlet valve 24 and is connected to and spring biased against a main body 70. Sliders 72 permit the outlet slider assembly 66 to be slidably associated with rails (not shown) within pump housing 48. A notch 74 is positioned on the main body 70 to provide a surface for transferring force from the motor 34 to the outlet control element 64.

Referring to FIGS. 1 and 7-10, a one-piece camshaft 76 is connected to shaft 36 and is thereby driven by the motor 34. The camshaft 76 has three lobes, with one lobe to drive the pumping element 38, inlet control element 52, and outlet control element 64. The camshaft 76 insures that the inlet and outlet valves 22 and 24 always will open and close at the appropriate times relative to the pumping element 38 stroke to achieve correct pump 10 operation.

A piston lobe 78 of the camshaft 76 is received within bore 50 of piston slider assembly 40. During rotation of camshaft 76, the piston lobe 78 pushes against bore 50 to drive piston slider assembly 40 back and forth within the pump housing 48. These movements result in piston head 42 intermittently pushing the pumping chamber 20 inward to drive fluid through cassette 12.

An inlet lobe 80 of the camshaft 76 contacts notch 62 of inlet slider assembly 54. During rotation of camshaft 76, the inlet lobe 80 pushes against notch 62 to drive inlet slider assembly 54 forward within the pump housing 48. These movements result in inlet pin 56 intermittently being compressed against the inlet valve 22 to cut off pumping chamber 20 from influent. Once the inlet lobe 80 releases this pressure on inlet pin 56, the spring biased compression force in inlet pin 56 is released against the main body 58, causing the main body 58 to retract from the inlet valve 22.

An outlet lobe 82 of the camshaft 76 contacts notch 74 of outlet slider assembly 66. During rotation of camshaft 76, the outlet lobe 82 pushes against notch 74 to drive outlet slider assembly 66 forward within the pump housing 48. These movements result in inlet pin 68 intermittently being compressed against the outlet valve 24 to cut off pumping chamber 20 from discharging effluent. Once the outlet lobe 82 releases this pressure on outlet pin 68, the spring biased compression force in outlet pin 68 is released against the main body 70, causing the main body 70 to retract from the outlet valve 24.

It will be understood by those skilled in the art, that the notches 62 and 74 and inlet and outlet lobes 80 and 82 associated therewith may be oriented and arranged so that the inlet and outlet lobes 80 and 82 move the inlet and outlet slider assemblies 54 and 56 back from cassette 12 without the assistance of spring biased pins 56 and 68.

The inlet and outlet lobes 80 and 82 operate to open and close inlet and outlet valves 22 and 24 at appropriate times to assure that there is unidirectional flow of the feeding liquid through the cassette 12. Because one or the other of the inlet and outlet slider assemblies 54 and 66 is in the closed position at any given point in the pumping element 38 stroke, they also prevent free flow of liquid through the cassette 12. In addition to preventing free flow, the inlet and outlet lobes 80 and 82 are designed to keep both of the inlet and outlet slider assemblies 54 and 66 in the closed position simultaneously during the first 35° of the pumping cycle, which permits relevant pressure data to be taken.

Referring to FIG. 1, a pressure sensor 84 is operatively associated with the pumping element 38. The pressure sensor 84 senses the force on pumping element 38 and generates a pressure signal based on this force. The pressure sensor 84 communicates with the processing unit 26, sending the pressure signal to the processing unit 26 for use in determining operating conditions of pump 10.

One of ordinary skill in the art will appreciate that the pressure sensor 84 may be a force transducer or any other device that can operatively sense the force brought to bear on the pumping chamber 20 by pumping element 38. The sensor 84 measures the force, which the pumping element 38 is pressing on the diaphragm 21. This force consists of two major components; the force required to displace the diaphragm 21 and the pressure of the fluid in the pumping chamber 20.

Referring to FIGS. 1, 4 and 5, the pressure sensor 84 is attached to the piston slider assembly 40. The pressure sensor 84 is connected directly between the piston head 42 and the main body 44. As the piston slider assembly 40 is brought to bear on the pumping chamber 20, the piston head 42 presses against pressure sensor 84. Pressure sensor 84 senses this force and generates a pressure signal to the processing unit 26.

Referring to FIG. 1, a position sensor 86 tracks the pumping cycle of pump 10 by determining the position of the pumping element 38. The position sensor 86 is shown as operatively associated with the shaft 36. The position sensor 86 generates a position signal by directly or indirectly detecting the position of the pumping element 38. The position signal is sent to the processing unit 26. The processing unit 26 utilizes this information to associate the incoming pressure data with a particular portion of the pump cycle. One of ordinary skill in the art will appreciate that the position sensor 86 as used herein includes but is not limited to mechanical indicators such as pivoting dial indicators, electronic switches, Hall Effect sensors, and optical based position detectors.

Figure 11:
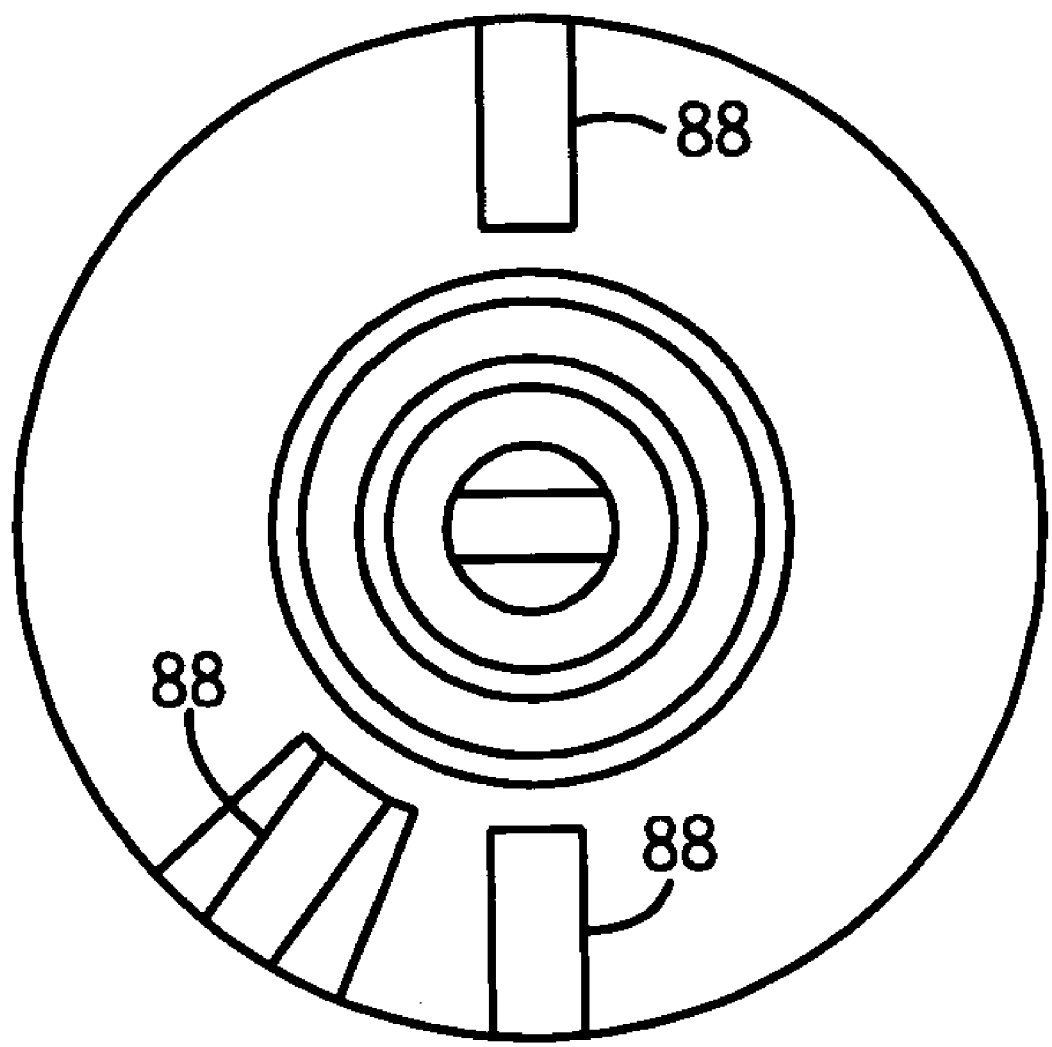
FIG. 11 is an end view of sensor magnets located on the camshaft of the pump of the present invention.

Referring to FIGS. 1, 4 and 11, the position sensor 86 is a Hall Effect sensor having magnets 88 in relational contact with shaft 36. The Hall Effect sensor 86 monitors the magnets 88 to determine the rotational position of shaft 36. The rotational position of shaft 36 is used to indirectly detect the position of the pumping element 38. The position sensor 86 communicates with the processing unit 26, sending the position signal to the processing unit 26 for use in determining operating conditions of pump 10. One of ordinary skill in the art will appreciate that the position sensor 86 can track the shaft 36, a camshaft 76 attached to the shaft 36, or the pumping element 38 itself.

Referring to FIG. 1, in operation, at the beginning of a pumping cycle, outlet control element 64 operates to close outlet valve 24 so that there is no fluid communication between pumping chamber 20 and outlet port 18. Inlet valve 22 is opened to permit pumping chamber 20 to be in fluid communication with inlet port 16. In the next phase of the pumping cycle, inlet control element 52 operates to close inlet valve 22, thereby closing fluid communication between inlet port 16 and pumping chamber 20. Outlet valve 24 continues to remain closed. Next, pumping element 38 begins a down-stroke movement which presses pumping element 38 against pumping chamber 20, causing pumping chamber 20 to compress, thereby increasing the pressure within pumping chamber 20. Pressure sensor 84 reads and transmits this pressure data to processing unit 26. Under normal conditions the pumping chamber 20 is compressed sufficiently and a desired pressure profile is generated. At a given position of the shaft 36, the outlet control element 64 operates to open outlet valve 24 so that fluid flows from pumping chamber 20 to outlet port 18. The pump cycle then repeats.

The processing unit 26 retrieves the operating condition algorithm 32 from memory 30 and applies it to the pressure and position data received from this pump cycle. The pump pressure data and pump position data are processed. Sensing the force that the pumping chamber 20 exerts against the pumping element 38 and comparing that force to what one would expect to sense at that point in the cycle can determine all of the following operating conditions: when flow of fluid is blocked (occlusion), there is no fluid in the line, there is no cassette in the pump, if the pump has primed correctly, and if the valve in the pump are sealing properly. Once the operating condition is determined, the processing unit 26 outputs the operating condition on the display 28 and/or uses the determined operating condition to adjust operation of the pump 10.

Figure 12:
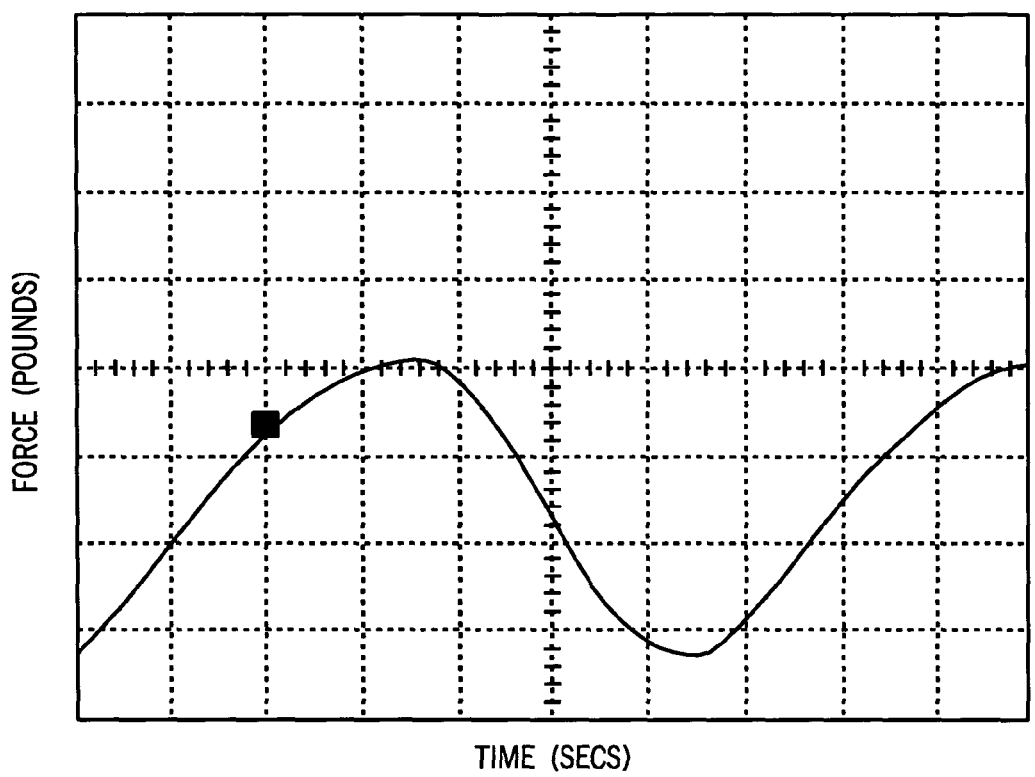
FIG. 12 is a graph showing force data from a pump cycle illustrating an abnormal air stroke.

Referring to FIG. 12, an exemplary force curve is shown where the pumping element 38 moves in essentially a constant cyclic (sine-wave) motion, the pumping element 38 always has sufficient force available so that its speed is essentially independent of the force applied to the pumping element 38, and the outlet flow from pumping chamber 20 is not restricted. This curve was generated using an off-the-shelf force sensor available from Strain Measurement Devices, Inc. (SMD) of Meriden, Conn., U.S.A. under part number 2508-020 S420. Currently a customized force sensor available from SMD under part number BAT2656 is preferred for its smaller size and overload protection. However, one skilled in the art will appreciate that selection or design of a particular force sensor is a matter of routine design choice based on the size constraints and the desired functional sensor characteristics. The curve starts at Bottom Dead Center (BDC) with the pumping element 38 deflecting the pumping chamber 20 about 0.10 inches (2.54 mm) at this point. As the pumping element 38 moves into the cassette 12 (which is called the down-stroke or output stroke because fluid is flowing out of the cassette 12) the force builds to a maximum at Top Dead Center (TDC), shown about ⅓ of the way along the curve. The pumping element 38 then moves out of the cassette 12 (which is called the up-stroke or inlet stroke because fluid is flowing into to cassette 12) and the force drops off until it is minimum at BDC again (about ⅔ of the way along the curve). This curve then shows another BDC to TDC stroke for the final ⅓ of the curve (showing 1.5 full cycles of pumping element 38 movement). The position sensor 86 allows the pump 10 to sense when the pumping element 38 should be at BDC, TDC, or about 35° past BDC.

In a prior art diaphragm pump, the inlet valve would close, and the outlet valve would open at BDC to allow flow of fluid out of the cylinder during the output stroke. The pump 10 of present invention, however, is altered so that the outlet valve 24 does not open until the pumping element 38 has completed part of its output stroke (at roughly 35° past BDC). If the cassette 12 is full of liquid during the output stroke, the movement of the pumping element 38 into the cassette 12 with both the inlet and outlet valves 22 and 24 closed will result in a significant rise in the pressure of the liquid, and thus the resulting force on the pumping element 38. If the pumping chamber 20 of the cassette 12 is partly full of air, the pressure rise will be significantly lower, because air is much more compressible than liquid. FIG. 12 shows the force curve generated with air in the pumping chamber 20.

Figure 13:
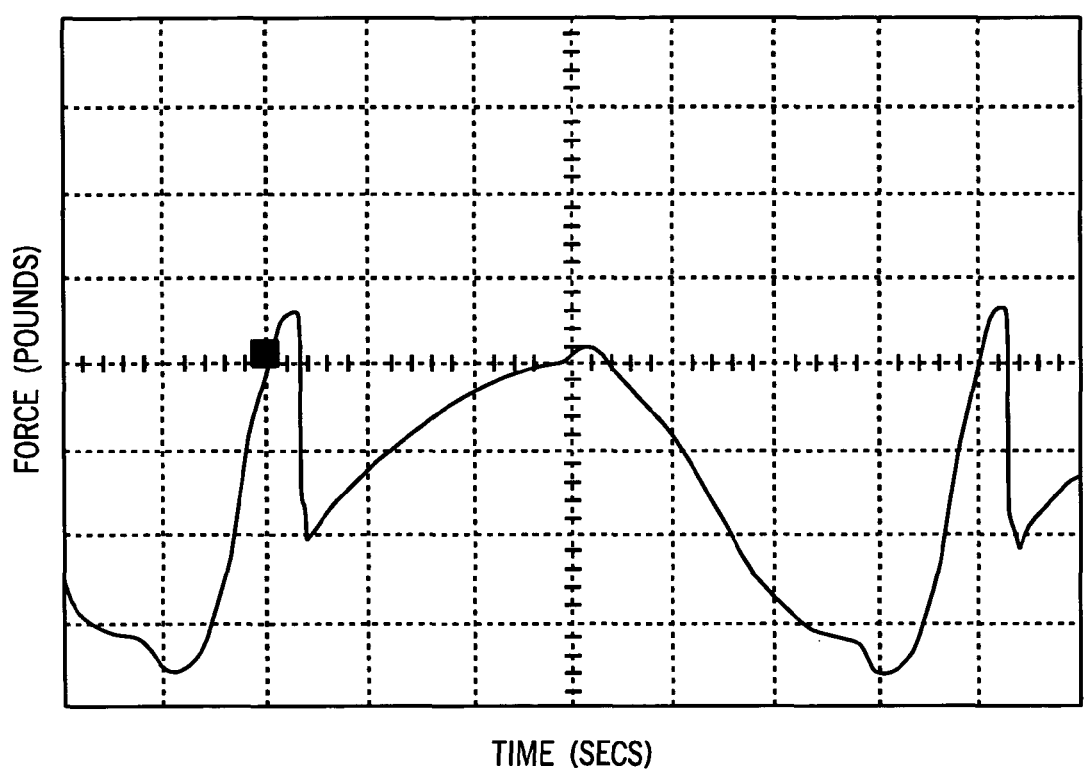
FIG. 13 is a graph showing force data from a pump cycle illustrating a normal fluid stroke.

Referring to FIG. 13, a force curve generated with the cassette 12 full of liquid (note that BDC is now shifted slightly to the right and does not occur at the far left edge of the force trace) is shown. The large spikes result from the buildup of pressure in the cassette 12 exerting significant force onto the pumping element 38. When the outlet valve 24 opens (about one-fourth of the way along this curve) the pressure immediately drops, and the force exerted on the pumping element 38 now is only that resulting from the partly stretched diaphragm 21 of the pumping chamber 20. The pressure starts to rise just about 35° past BDC and the magnets 88 at that position provides a signal to allow the pump 10 to start taking data. By examining the force curve one can deduce whether the cassette 12 was full of liquid (i.e. a fluid stroke and exemplified by FIG. 13), or if the cassette 12 contained a significant amount of air (called an air stroke and exemplified by FIG. 12).

The processing unit 26 executes algorithm 32 to electronically examine the force curve and makes the determination of whether it is a fluid or air stroke. The result of this algorithm 32 produces a number called the Figure of Merit. If the Figure of Merit is above a threshold value of 450, the pump interprets this as a fluid stroke; below 450, as an air stroke. One of ordinary skill in the art will understand that these threshold values are predetermined empirically from experimental data, and will vary from pump model to pump model.

Pump 10 also has an automatic priming feature, to determine if the pump 10 has been automatically primed correctly or if it has failed to do so. When the cassette 12 is installed in the pump 10, the pump 10 primes the feeding tube set (not shown) attached to the cassette 12. The initial strokes of the pump 10 during priming will be recorded as air strokes because the liquid from the feeding tube set (not shown) has not yet reached the pumping chamber 20 in the cassette 12. If too many of these air strokes are recorded before fluid strokes are sensed, this is interpreted by the processing unit 26 as the pump 10 having failed to prime properly, and an appropriate alarm is provided to display 28 or otherwise. If the pump 10 records fluid strokes within the specified number of strokes, then the processing unit 26 knows that the cassette 12 has been primed successfully.

Figure 14:
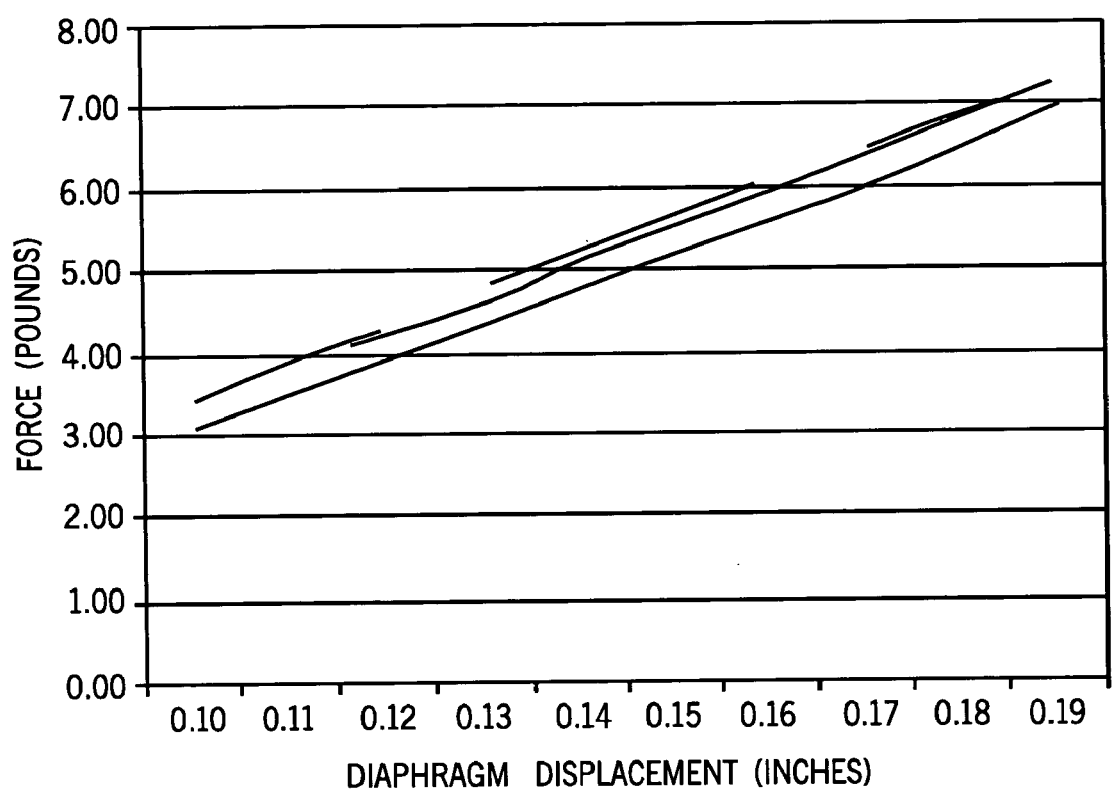
FIG. 14 is a graph showing force data illustrating the presence and absence of a cassette in the pump.

Referring to FIG. 14, pump 10 also determines if there is no cassette 12 in the pump 10. The diaphragm 21 of the pump chamber 20 of cassette 12 installed in the pump 10 will produce a certain amount of force on the pumping element 38. FIG. 14 shows the results of testing four cassettes to determine their force vs. deflection characteristics. About 0.10 inches (2.54 mm) of diaphragm 21 displacement is expected if a cassette 12 is installed in the pump 10. The force curve is examined to make sure that during a stroke, some minimum amount of force is registered on the pressure sensor 84. If this condition is not satisfied, the processing unit 26 interprets this to mean that no cassette 12 was installed in the pump 10 and an appropriate alarm is provided to display 28 or otherwise. A cassette out alarm may also be provided where the pressure sensor 84 fails to produce an output voltage.

Figure 15:
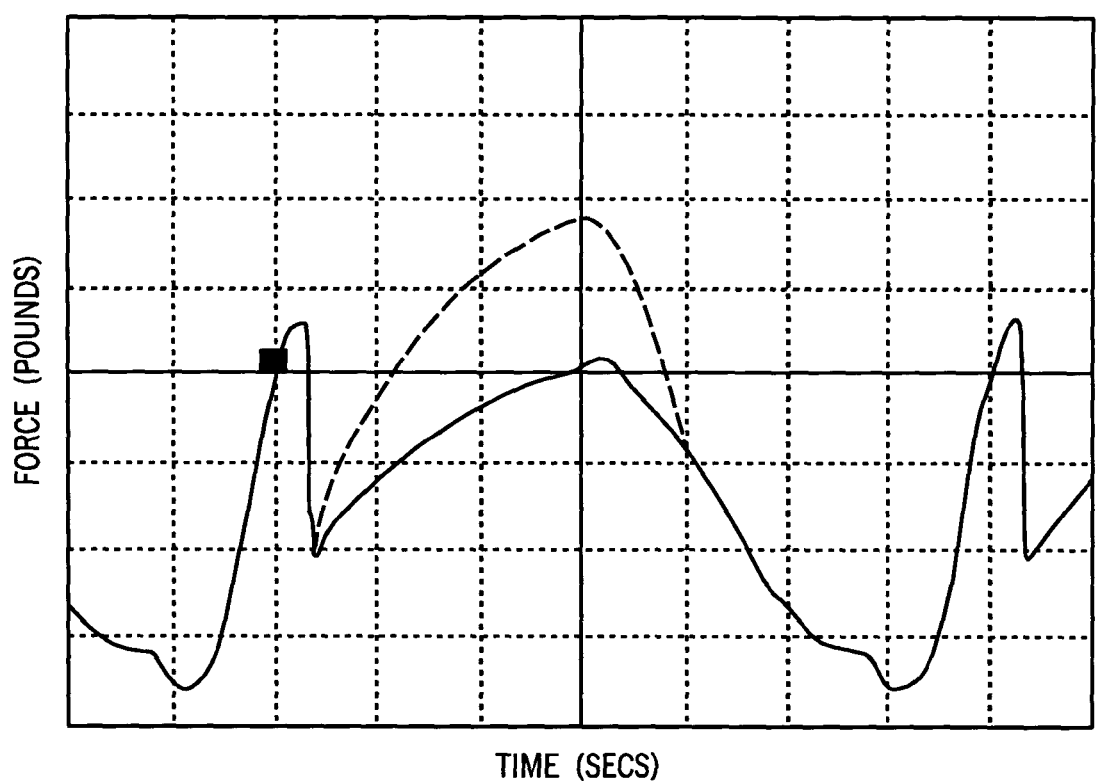
FIG. 15 is a graph showing force data from a pump cycle illustrating impeded outlet flow.

Referring to FIG. 15, by examining the force curve near TDC, the processing unit 26 can determine if the flow of fluid is blocked to the patient. The pressure on the pumping element 38 is the sum of the force exerted on the pumping element 38 by the diaphragm 21 (see FIG. 14) and the force on the pumping element 38 due to the pressure load. In normal operation the pressure is very low because the flow out of the cassette 12 is unimpeded. However, if the outlet flow is impeded by a significant restriction downstream of the outlet 18, the pressure will increase significantly near TDC as illustrated by the dashed line in FIG. 15. If that pressure is sufficiently large, the processing unit 26 generates a signal or alarm indicating that a flow blocked (occlusion) condition exists to display 28 or otherwise. It should be noted that the blocked flow alarm is sounded and/or displayed, even though some fluid flow may continue.

Once the pump 10 is in normal operation (i.e., pumping fluid) and the pressure sensor 84 registers four consecutive air strokes, the processing unit 26 interprets this condition as a bag empty condition. The processing unit 26 generates a bag empty alarm to display 28 or otherwise.

If one or both inlet and outlet slider assemblies 54 and 66 are not pressing the cassette 12 in such a manner as to cause a proper seal, the pressure spike will be suppressed. The suppressed pressure spike will result in a reduction in the calculated Figure of Merit. The processing unit 26 interprets this condition as an improper valve seal condition, and generates an alarm to display 28 or otherwise notifies the user of the pump 10. It is important to detect this condition because the pump 10 can over deliver under certain conditions if the inlet and outlet slider assemblies 54 and 66 do not produce a proper seal.

Figure 16:
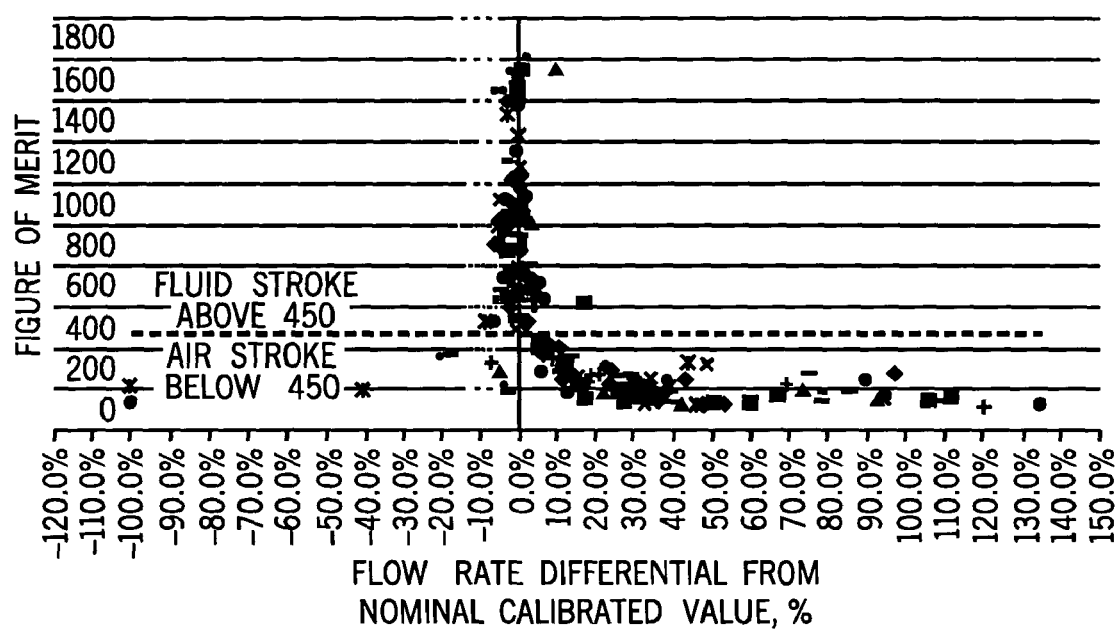
FIG. 16 is a graph showing flow rate test data taken with a wide range of cassettes and pumps employing the present invention.

Referring to FIG. 16, test data taken with a wide range of cassettes and four different pumps is shown. This data shows that as long as the pump 10 is producing a Figure of Merit number that is interpreted by processing unit 26 to be a fluid stroke, the pump 10 will be producing a flow rate within about 10% of its calibrated value. Thus the pump 10 will not be over or under delivering a significant amount of fluid, so long as processing unit 26 determines fluid stroke conditions are met.

Whereas the invention has been shown and described in connection with the embodiments thereof, it will be understood that many modifications, substitutions, and additions may be made which are within the intended broad scope of the following claims. From the foregoing, it can be seen that the present invention accomplishes at least all of the stated objectives.

We claim:

1. A medical pump for use with a cassette having a pumping chamber, comprising:
   a pumping element adapted to forcibly press on and intermittently pressurize the pumping chamber during a pumping cycle, wherein the pumping element includes a piston head connected to a main body;
   means for closing the pumping chamber to flow during at least a portion of the pump cycle when the pumping chamber is pressurized by the pumping element; and
   a single pressure sensor operatively connected to the pumping element to detect the pressure exerted by the pumping element on the pumping chamber, the single pressure sensor rigidly connected in a force bearing relationship to at least one of the piston head and the main body.

2. The medical pump of claim 1, wherein said means includes an inlet control element and an outlet control element adapted to close the pumping chamber to flow during at least a portion of the pump cycle when the pumping chamber is pressurized by the pumping element; and a camshaft associated with the pumping element, inlet control element, and outlet control element for closing the pumping chamber to flow during at least a portion of the pump cycle when the pumping chamber is pressurized by the pumping element.

3. The medical pump of claim 1, further including a processing unit in electronic communication with the pressure sensor, wherein the processing unit processes pressure data from the pressure sensor to determine the operating condition of the pump.

4. The medical pump of claim 3, wherein the operating condition determined is blocked fluid flow, no fluid in the line, no cassette associated with the pump, proper pump priming, or proper valve sealing.

5. The medical pump of claim 3, further including a position sensor in electronic communication with the processing unit and operatively associated with the pumping element to detect the position of the pumping element, wherein the processing unit processes position data from the position sensor to associate the incoming pressure data with a particular portion of the pump cycle.

6. A medical pump for use with a cassette having a pumping chamber, comprising:
   a pumping element including a piston slider assembly adapted to intermittently pressurize and forcibly press on the pumping chamber during a pumping cycle, the piston slider assembly having a piston head connected to a main body, the piston head adapted to contact the pumping chamber; and
   a single pressure sensor rigidly connected to the pumping element in a force bearing relationship with the piston head and the main body to directly detect the pressure exerted by the pumping element on the pumping chamber.

7. The medical pump of claim 6, wherein the piston slider assembly includes a bore which passes through the main body and provides a surface for transferring force from a pump motor to the pumping element.

8. The medical pump of claim 6, wherein the piston slider assembly includes slider elements which permit the piston slider assembly to be slidably associated with a pump housing.

9. The medical pump of claim 6, further including a processing unit in electronic communication with the pressure sensor, wherein the processing unit processes pressure data from the pressure sensor to determine the operating condition of the pump.

10. The medical pump of claim 9, wherein the operating condition determined is blocked fluid flow, no fluid in the line, no cassette associated with the pump, proper pump priming, or proper valve sealing.

11. The medical pump of claim 9, further including a position sensor in electronic communication with the processing unit and operatively associated with the pumping element to detect the position of the pumping element, wherein the processing unit processes position data from the position sensor to associate the incoming pressure data with a particular portion of the pump cycle.

12. The medical pump of claim 6, further including means for closing the pumping chamber to flow during at least a portion of the pump cycle when the pumping chamber is pressurized by the pumping element.

13. The medical pump of claim 6, further including an inlet control element and an outlet control element adapted to close the pumping chamber to flow during at least a portion of the pump cycle when the pumping chamber is pressurized by the pumping element; and a camshaft associated with the pumping element, inlet control element, and outlet control element for closing the pumping chamber to flow during at least a portion of the pump cycle when the pumping chamber is pressurized by the pumping element.

14. The medical pump of claim 6, wherein the pressure sensor is a force sensor and is the only pressure sensor included in the medical pump.

15. A medical pump for use with a cassette having a pumping chamber, comprising:
   a pumping element adapted to intermittently pressurize and to press on the pumping chamber during a pumping cycle, wherein the pumping element includes a piston slider assembly having a piston head connected to a main body, the piston head adapted to contact the pumping chamber;
   an inlet control element and an outlet control element adapted to close the pumping chamber to flow;
   a camshaft associated with the pumping element, inlet control element, and outlet control element for closing the pumping chamber to flow during at least a portion of the pump cycle when the pumping chamber is pressurized by the pumping element; and
   a single pressure sensor operatively connected to the pumping element to detect the pressure exerted by the pumping element on the pumping chamber, the single pressure sensor rigidly connected to the piston slider assembly in a force bearing relationship with at least one of the piston head and the main body.

16. The medical pump of claim 15, further including a processing unit in electronic communication with the pressure sensor, wherein the processing unit processes pressure data from the pressure sensor to determine the operating condition of the pump.

17. The medical pump of claim 16, wherein the operating condition determined is blocked fluid flow, no fluid in the line, no cassette associated with the pump, proper pump priming, or proper valve sealing.

18. The medical pump of claim 16, further including a position sensor in electronic communication with the processing unit and operatively associated with the pumping element to detect the position of the pumping element, wherein the processing unit processes position data from the position sensor to associate the incoming pressure data with a particular portion of the pump cycle.

19. The medical pump of claim 15, wherein the pressure sensor is the only pressure sensor included in the medical pump.

20. The medical pump of claim 19, wherein the pressure sensor is a force sensor.

* * * * *